US009986915B2

(12) United States Patent
Carr et al.

(10) Patent No.: US 9,986,915 B2
(45) Date of Patent: Jun. 5, 2018

(54) SYSTEMS AND METHODS FOR A SHORT WAVE INFRARED DEVICE

(71) Applicant: MASSACHUSETTS INSTITUTE OF TECHNOLOGY, Cambridge, MA (US)

(72) Inventors: Jessica Carr, Fairmont, WV (US); Oliver Bruns, Boston, MA (US); Moungi Bawendi, Cambridge, MA (US); Tulio Valdez, Simsbury, CT (US)

(73) Assignee: Massachusetts Institute of Technology, Boston, MA (US)

( * ) Notice: Subject to any disclaimer, the term of this patent is extended or adjusted under 35 U.S.C. 154(b) by 0 days. days.

(21) Appl. No.: 15/221,517

(22) Filed: Jul. 27, 2016

(65) Prior Publication Data

US 2017/0027448 A1    Feb. 2, 2017

Related U.S. Application Data

(60) Provisional application No. 62/199,126, filed on Jul. 30, 2015.

(51) Int. Cl.
| | |
|---|---|
| *A61B 1/00* | (2006.01) |
| *A61B 1/06* | (2006.01) |
| *A61B 1/07* | (2006.01) |
| *A61B 1/227* | (2006.01) |
| *A61B 1/32* | (2006.01) |

(Continued)

(52) U.S. Cl.
CPC ........ *A61B 5/0086* (2013.01); *A61B 1/00009* (2013.01); *A61B 1/0646* (2013.01); *A61B 1/0684* (2013.01); *A61B 1/07* (2013.01); *A61B 1/227* (2013.01); *A61B 1/32* (2013.01); *A61B 5/12* (2013.01); *A61B 5/7282* (2013.01)

(58) Field of Classification Search
CPC . A61B 1/00009; A61B 1/0646; A61B 1/0648; A61B 1/0684; A61B 1/07; A61B 1/227; A61B 1/32; A61B 1/043; A61B 1/00045; A61B 1/0638; G01N 21/65; G01J 3/44; G01J 3/4406; G01B 9/02004; G01B 9/02044; G01B 9/0205; G01B 9/02091; G01B 9/02014; G01B 9/02083
USPC ......... 600/476, 316, 178, 437; 356/479, 497
See application file for complete search history.

(56) References Cited

U.S. PATENT DOCUMENTS

2003/0204133 A1    10/2003  Harjunmaa et al.
2005/0273011 A1*   12/2005  Hattery ............... A61B 5/0059
                                              600/476

(Continued)

FOREIGN PATENT DOCUMENTS

WO    WO2013160780 A1    10/2013

OTHER PUBLICATIONS

PCT International Search Report and Written Opinion, PCT/US2016/044333, dated Oct. 18, 2016.

*Primary Examiner* — Pedro Philogene
(74) *Attorney, Agent, or Firm* — Quarles & Brady LLP

(57) ABSTRACT

Systems and methods for a short wave infrared (SWIR) otoscope device are provided. The SWIR otoscope device can capture images of a patient's middle ear to aid in diagnosing one of a plurality of maladies. In one embodiment, the SWIR otoscope device can include a SWIR detector, a light source, and a plurality of optics that can enable the SWIR otoscope device to capture images of the middle ear of a patient.

37 Claims, 7 Drawing Sheets

(51) Int. Cl.
*A61B 5/00* (2006.01)
*A61B 5/12* (2006.01)

(56) References Cited

U.S. PATENT DOCUMENTS

| | | | |
|---|---|---|---|
| 2008/0208006 A1* | 8/2008 | Farr | A61B 1/0607 600/178 |
| 2009/0185191 A1* | 7/2009 | Boppart | A61B 5/0066 356/479 |
| 2016/0007857 A1* | 1/2016 | Wang | A61B 5/0073 600/425 |
| 2017/0071509 A1* | 3/2017 | Pandey | A61B 5/12 |

* cited by examiner

SYSTEMS AND METHODS FOR A SHORT WAVE INFRARED DEVICE

CROSS-REFERENCES TO RELATED APPLICATIONS

The present application is based on, claims priority to, and incorporates herein by reference in its entirety, U.S. Provisional Patent Application No. 62/199,126, filed Jul. 30, 2015, and entitled "Systems and Methods for a Short Wave Infrared Device."

STATEMENT REGARDING FEDERALLY SPONSORED RESEARCH

This invention was made with government support under Grant No. P41 EB015871 awarded by the National Institutes of Health and under Contract No. W911NF-13-D-0001 awarded by the Army Research Office. The government has certain rights in the invention.

BACKGROUND

The disclosure relates generally to a medical device and methods of use and, more specifically, to a short-wave infrared device capable of providing images and aiding in diagnosing of maladies, for example, within a patient's ear.

Otitis media, a range of inflammatory conditions of the middle ear, is the second most common illness diagnosed in children. However, identifying the presence of middle-ear fluid is challenging in pediatric patients, resulting in a high rate of over-diagnosis and indiscriminant use of antibiotics. In addition to otitis media, challenges in monitoring the ossicular chain and/or cholesteatoma extension in the middle ear of a patient may lead to the patient experiencing hearing loss without proper diagnosis.

BRIEF SUMMARY

The present disclosure provides systems and methods for a short wave infrared (SWIR) otoscope device that can capture images of a patient's middle ear to aid in diagnosing one of a plurality of maladies. In one non-limiting example, the SWIR otoscope device can include a SWIR detector, a light source, and a plurality of optics which enable the SWIR otoscope device to capture images of the middle ear of a patient.

In one aspect, the present disclosure provides a short wave infrared otoscope device including a light source configured to emit short wave infrared light along an optical path through a speculum to illuminate a portion of a patient's ear with short wave infrared light, a short wave infrared detector configured to be coupled to a speculum adapter to capture an image of the portion of the patient's ear, and an optical system arranged between the speculum and the short wave infrared detector. The optical system includes a lens.

In another aspect, the present disclosure provides a short wave infrared retrofit kit for an otoscope having a speculum received within a speculum adapter. The short wave infrared retrofit includes a light source configured to emit short wave infrared light through the speculum, a short wave infrared detector configured to be coupled to the speculum adapter and arranged to view through the speculum, and an optical system arranged between the speculum and the short wave infrared detector. The optical system includes a lens.

In yet another aspect, the present disclosure provides a method for using a short wave infrared device to detect a malady of a patient's ear. The short wave infrared device includes a light source, a short wave infrared detector arranged to view along an optical path and an optical system arranged to view along the optical path. The method includes positioning the short wave infrared device to view within the patient's ear, emitting short wave infrared light along the patient's ear canal via the light source, and illuminating a portion of the patient's ear via the emitted short wave infrared light. The method further includes capturing an image, using the short wave infrared detector, of the reflected light from the illuminated portion of the patient's ear, and detecting the malady of the patient's ear based on an abnormality in the captured image.

In still another aspect, the present disclosure provides a method for retrofitting an otoscope with a short wave infrared retrofit kit. The otoscope includes a speculum received within a speculum adapter. The method includes coupling a light source to the speculum adapter. The light source is configured to emit short wave infrared light through the speculum. The method further includes coupling a short wave infrared detector to the speculum adapter. The short wave infrared detector is arranged to view through the speculum. The method further includes arranging an optical system between the speculum and the short wave infrared detector. The optical system including a lens.

In yet another aspect, the present disclosure provides a method for detecting fluid in a middle ear of a patent. The method includes illuminating a portion of the patient's ear with short wave infrared light, and detecting light reflected from the portion of the patients ear with a short wave infrared detector and acquiring an image of the detected light. The method further includes measuring a light intensity of a superficial anatomical structure in the acquired image, measuring a light intensity of a deep anatomical structure in the acquired image, and calculating an intensity ratio between the light intensity of the superficial anatomical structure and the light intensity of the deep anatomical structure. The method further includes determining if the calculated intensity ratio is above a predetermined threshold value, and upon determining that the calculated intensity ratio is above the predetermined threshold value, detecting a presence of fluid in the middle ear of the patient.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF DRAWINGS

The invention will be better understood and features, aspects and advantages other than those set forth above will become apparent when consideration is given to the following detailed description thereof. Such detailed description makes reference to the following drawings.

DETAILED DESCRIPTION

The term "visible light" as used herein refers to a portion of the electromagnetic spectrum, generally bound between wavelengths of approximately 380 nanometers (nm) and 750 nm, that is visible to the human eye. One of skill in the art would recognize that the wavelength range of visible light will vary from person to person depending on one's vision. Thus, the range from 380 nm to 750 nm is a generally accepted range and is not meant to be definitively limiting in any way.

The term "short wave infrared (SWIR) light" as used herein refers to a portion of the electromagnetic spectrum generally bound between wavelengths of approximately 800 nm and 2000 nm. The SWIR light range from 800 nm to 2000 nm is a generally accepted range and is not meant to be definitively limiting in any way.

Currently, pneumotoscopy is used to attempt to detect the presence of middle ear fluid. Pneumotoscopy involves using a pneumatic otoscope to apply air pressure to a patient's eardrum to attempt to detect displacement, with displacement signifying no middle ear fluid and no displacement signifying the presence of middle ear fluid. This process is qualitative and significantly operator-dependent, and can suffer in both sensitivity and in specificity with an inexperienced practitioner. Another diagnostic performed on a patient's ear is monitoring of the ossicular chain and/or cholesteatoma extension. Currently, monitoring a patient's ossicular chain and/or cholesteatoma extension utilizes expensive, potentially harmful, and time consuming radiographic procedures.

Due to the current difficulties in quickly and accurately imaging the middle ear of a patient to diagnose a plurality of potential maladies, it would be desirable to have a retrofit kit for an otoscope that could be easily integrated into the otoscope and enable the otoscope to capture images of a patient's middle ear to provide an unambiguous assessment of the health of the patient's middle ear.

Figure 1:
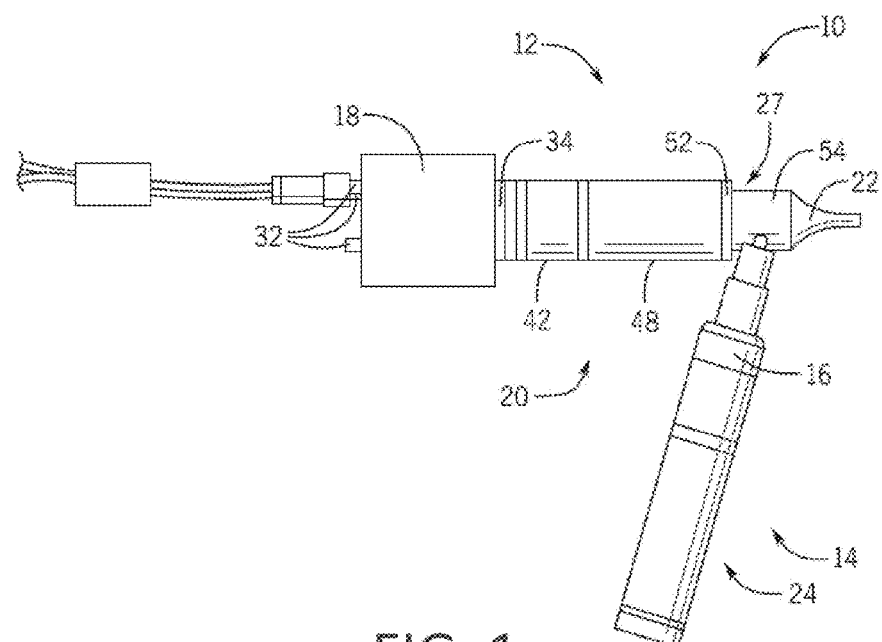
FIG. 1 shows a short wave infrared otoscope device in accordance with one embodiment of the present disclosure.
Figure 2:
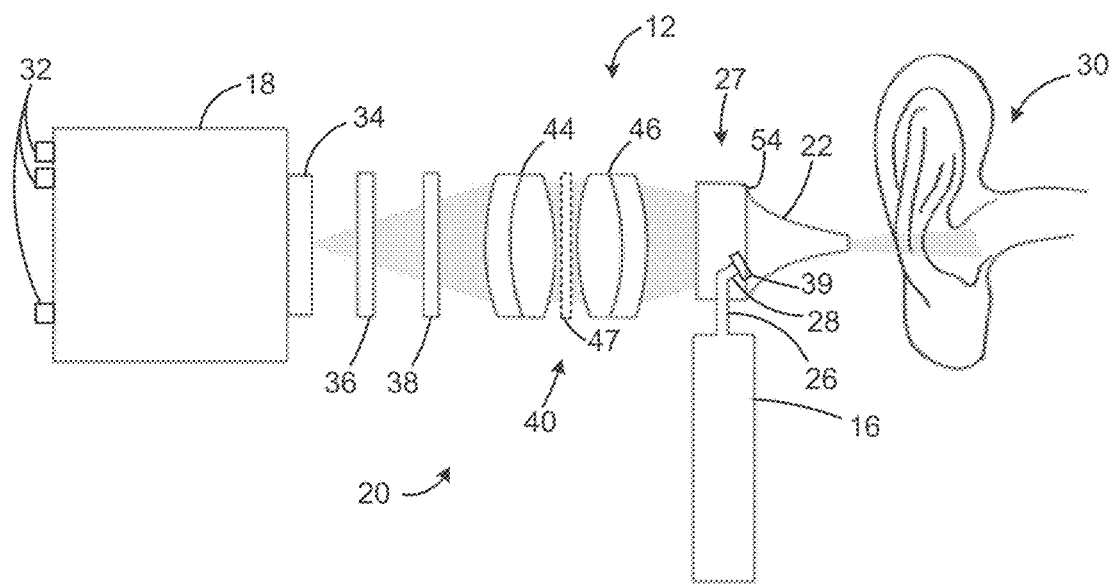
FIG. 2 shows a schematic of a retrofit kit of the short wave infrared otoscope device in accordance with one embodiment of the disclosure.

FIG. 1 shows one non-limiting example of a short wave infrared (SWIR) otoscope device 10 in accordance with the present disclosure. As shown in FIGS. 1 and 2, the SWIR otoscope device 10 includes a SWIR retrofit kit 12 that can be integrated into an otoscope 14. The SWIR retrofit kit 12 includes a light source 16, a SWIR detector 18, and a plurality of optics or an optical system 20 arranged between the SWIR detector 18 and a speculum 22 of the otoscope 14. The SWIR retrofit kit 12 can enable the otoscope 14 to view and/or capture images of a patient's ear typically blocked by the tympanic membrane, as will be described in detail below.

The light source 16 is configured to emit SWIR light. SWIR light can penetrate deeper within human tissue when compared to visible light and, therefore, a greater amount of the SWIR light emitted by the light source 16 can penetrate through the tympanic membrane in the patient's ear without being reflected, scattered, and/or absorbed (i.e., attenuated). The penetration of SWIR light through the tympanic membrane enables light source 16 to illuminate the patient's middle ear anatomy (e.g., malleus, promontory, round window, incudostapedial complex, chorda tympani, etc.). In one non-limiting example, the light source 16 can be an incandescent or halogen tungsten light source configured to emit broadband SWIR light in a wavelength range between approximately 800 nm and 2000 nm. In this non-limiting example, a source narrow band-pass filter (not shown), configured to transmit light in a specific wavelength range, can be used to narrow the wavelength range emitted by the light source 16. For example, a center wavelength of the wavelength range transmitted by the source narrow-band pass filter may be 950 nm, 1050 nm, 1300 nm, or 1450 nm.

In another non-limiting example, the light source 16 can include one or more light emitting diodes (LEDs). The LEDs can all be configured to output light in the same wavelength band, or the LEDs can be individually operated and configured to output light at different wavelengths. For example, in one non-limiting example, the light source 16 can include individually operated LEDs configured to output light at approximately 950 nm, approximately 1050 nm, approximately 1300 nm, and approximately 1450 nm.

In one non-limiting example, the light source 16 can be arranged within a handle 24 of the otoscope 14, as shown in FIG. 1. In one non-limiting example, the light source 16 can be fiber-coupled, and include a fiber optic cable 26 configured to efficiently transmit light emitted from the light source 16. The fiber optic cable 26 can be coupled to a speculum adapter 27 of the otoscope 14 and arranged such that light emitted from a distal end 28 of the fiber optic cable 26 is directed through the speculum 22 and into a patient's ear 30, as shown in FIG. 2. In another non-limiting example, the light source 16 can be arranged outside or separately from the handle 24 of the otoscope 14.

The SWIR detector 18 is configured to detect and capture images, or video, of SWIR light which transmits through the optical system 20. In one non-limiting example, the SWIR detector 18 can be an Indium Gallium Arsenide (InGaAs) detector with a 320 by 256 pixel array. One of skill in the art would recognize that other detectors may be used to detect SWIR light. The SWIR detector 18 includes one or more input/output (I/O) ports 32 and a lens tube adapter 34. The I/O ports 32 enable the SWIR detector 18 to be connected, for example via coaxial cables, to an external computing device, as will be described below. The lens tube adapter 34 enables the SWIR detector 18 to be fastened to an optomechanical element (e.g., a lens tube, a lens mount, an extension tube, a filter holder, etc.).

With continued reference to FIGS. 1 and 2, the optical system 20 can include a filter 36, a first polarizer 38, a second polarizer 39, and a lens 40. The filter 36 can be fixed within a filter holder 42 that is coupled to the lens tube adapter 34 of the SWIR detector 18. In the illustrated non-limiting example, only one filter 36 may be used. The filter 36 can be a short pass filter, a long pass filter, or a band pass filter, depending on the desired operation of the SWIR otoscope device 10. In one non-limiting example, the filter 36 can be a long pass filter configured to allow light with a wavelength of greater than approximately 1300 nm to transmit through the filter 36 to the SWIR detector 18. In another non-limiting example, the filter 36 can be a band pass filter configured to allow light with a wavelength between approximately 1300 nm and 1700 nm to transmit through the filter 36 to the SWIR detector 18. In yet another non-limiting example, the filter 36 can be a band pass filter with a center wavelength of between approximately 1200 nm and 1220 nm. One of skill in the art will appreciate that alternative transmission ranges are possible for the filter 36 depending on the desired detection characteristics of the SWIR otoscope device 10.

The filter holder 42 enables the filter 36 to be easily exchanged during use of the SWIR otoscope for various applications. Regardless of the specific configuration of the filter 36, as will be described, the use of the filter 36 provides the basis to create an optical system 20 that can be integrated with and/or created as retrofit kit that can be coupled to the otoscope 14. That is, the system described herein provides an assembly that can be integrated with or retrofitted with an otoscope to provide a clinical tool that accommodates current analysis tools and clinical protocols.

The first polarizer 38 and the second polarizer 39 are configured to suppress unwanted reflections and glare detected by the SWIR detector 18. The first polarizer 38 is arranged adjacent to and along an optical path viewed by the SWIR detector 18 and the second polarizer 39 is arranged adjacent to the distal end 28 of the fiber optic cable 26. The second polarizer 39 polarizes the light emitted by the light source 16 and then, by crossing (i.e., rotating) the first polarizer 38 with respect to the second polarizer 39, the first polarizer 38 can filter or eliminate the polarized, directly reflected light from the light source 16 before being detected by the SWIR detector 18. Alternatively, if desired, the first polarizer 38 and the second polarizer 39 can be oriented in parallel (i.e., in the same rotational orientation) to allow directly reflected light from the light source 16, rather than diffuse light, to be detected by the SWIR detector 18. Thus, the relative orientation of the first and second polarizers 38 and 39 can be adjusted to selectively transmit or suppress reflected light from the light source 16. In one non-limiting example, the first polarizer 38 and/or the second polarizer 39 can be a near-infrared linear polarizer operable in a wavelength range between approximately 1000 nm and 2000 nm. In another non-limiting example, the optical system 20 may include only the first polarizer 38 and the second polarizer 39 may be excluded. In this non-limiting example, the first polarizer 38 can still suppress reflections and glare, although less efficiently than the configuration using the first polarizer 38 and the second polarizer 39, described above.

The lens 40 includes a first lens 44 and a second lens 46 that combine to form a near-infrared achromatic lens pair. In one non-limiting example, the first lens 44 can have an effective focal length of 100 millimeters (mm) and the second lens can have an effective focal length of 75 mm. The first lens 44 and the second lens 46 can be coated with a near-infrared anti-reflection coating that reduces or eliminates reflections of SWIR light. That is, the lens 40 enables a high throughput (i.e., transmission) of SWIR light to the SWIR detector 18. In one non-limiting example, the optical system 20 can include an iris 47 arranged between the first lens 44 and the second lens 46 of the lens 40. The addition of the iris 47 may improve a depth of field detected by the SWIR detector 18.

The first polarizer 38 and the lens 40 can be mounted in a lens tube 48 with the first polarizer 38 arranged between the lens 40 and the filter 36. It should be known that the orientation of the filter 36, the first polarizer 38, and the lens 40, shown in FIG. 2, is not meant to be limiting in any way and other configurations/orientations are within the scope of the present disclosure. For example, the filter 36 may be arranged between the first polarizer 38 and the lens 40, or the lens 40 may be arranged between the filter 36 and the first polarizer 38, etc. The lens tube 48 can be coupled to the filter holder 42 and the speculum adapter 27 of the otoscope 14. The speculum adapter 27 includes a lens tube adapter 52 for coupling the lens tube 48 to the otoscope 14, and an aperture 54. The aperture 54 is configured to receive the speculum 22, which is typically a disposable component that can be replaced after every use of the SWIR otoscope device 10 to prevent cross contamination between patients. In some non-limiting examples, the aperture 54 can receive disposable specula sized to be 2.5 mm, 3.0 mm, 4.0 mm, and/or 5.0 mm. The size of the speculum 22 is merely provided by way of example and is not meant to be limiting in any way.

Assembly of the SWIR otoscope device 10 will be described with reference to FIGS. 1 and 2. As described above, the SWIR otoscope device 10 includes the SWIR retrofit kit 12 and the otoscope 14. In one non-limiting example, the otoscope 14 can be a stock or traditional pneumatic otoscope that is modified in the following way to incorporate the SWIR retrofit kit 12. As such, and as further described herein, a clinical tool is provided that accommodates current analysis tools and clinical protocols. That is, an entirely new or different otoscope is not required, and the system described herein readily accommodates current clinical protocols. In one non-limiting example, the light source 16 can be built-in to the otoscope 14, typically into the handle 24. In another non-limiting example, the stock built-in light source of the otoscope 14 may not be configured to emit SWIR light and the light source 16 can be installed into the handle 24 of the otoscope 14 upon removal of the stock built-in light source.

As is known in the art, the stock otoscope 14 can include a lens coupled to the speculum adapter 27, which enables a medical professional to view through the speculum 22 and into a patient's ear. However, the stock lens is not configured to magnify/focus the SWIR light to form a focused image on the SWIR detector 18. Therefore, the stock lens can be removed and the lens tube adapter 52 can then be fastened to the speculum adapter 27. The lens tube 48 including the lens 40 and the first polarizer 38 can then be fastened to the lens tube adapter 52. The filter holder 42 including the filter 36 can then be fastened to the lens tube 48 and, lastly, the lens tube adapter 34 of the SWIR detector 18 can be fastened to the filter holder 42 thereby completing the integration of the SWIR retrofit kit 12 into the otoscope 14.

The lens tube adapter 52, the lens tube 48, the filter holder 42, and the lens tube adapter 34 optically align the SWIR detector 18 and the optical system 20 on a common optical path that extends through the speculum 22. This ensures that the SWIR detector 18 remains arranged to view through the speculum 22 throughout continuous assembly and disassembly of the SWIR otoscope device 10. Additionally, the lens tube 48, the filter holder 42, and the lens tube adapter 34 enable the SWIR detector 18, the filter 36, the first polarizer 38, and the lens 40 to be coupled together as a single unit. Alternative to the "piece-by-piece" assembly described above, the SWIR detector 18, the filter 36, the first polarizer 38, and the lens 40 may be fastened to the lens tube adapter 52 of the speculum adapter 27 as the single unit. Furthermore, the lens tube adapter 52, the lens tube 48, the filter holder 42, and the lens tube adapter 34 enable the SWIR retrofit kit 12 to be modular and easily change between alternative filters, lenses, polarizers, and/or detectors.

Figure 3:
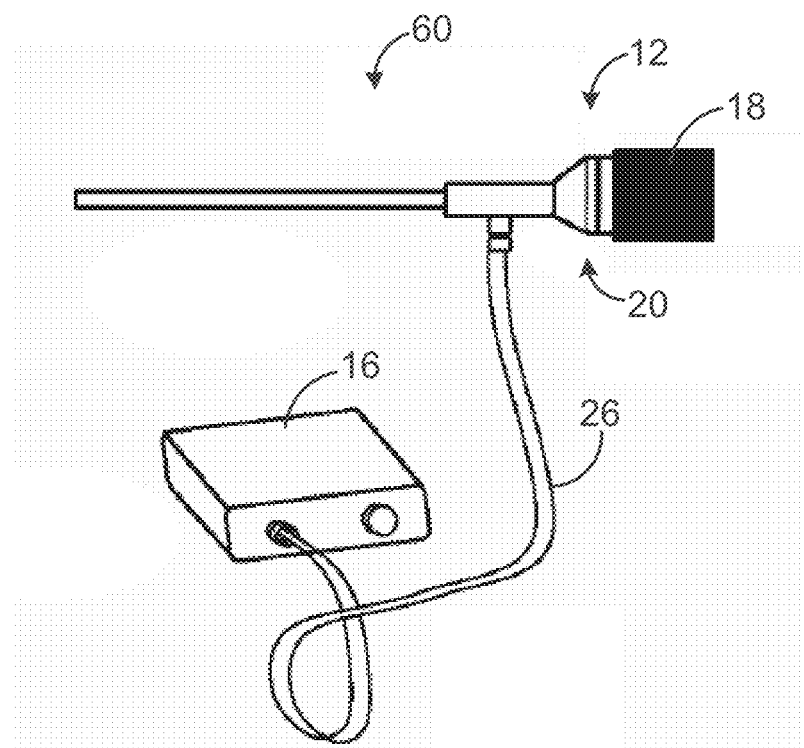
FIG. 3 shows a short wave infrared endoscope device in accordance with another embodiment of the present disclosure.

As described above, the components and construction of the SWIR retrofit kit 12 allow integration of the SWIR retrofit kit 12 into an otoscope 14 with limited modifications to the otoscope 14. It should be appreciated that the SWIR retrofit kit 12 may, in other non-limiting examples, be integrated into other medical devices. For example, as shown in FIG. 3, the SWIR retrofit kit 12 can be integrated into an endoscope 60.

Figure 4:
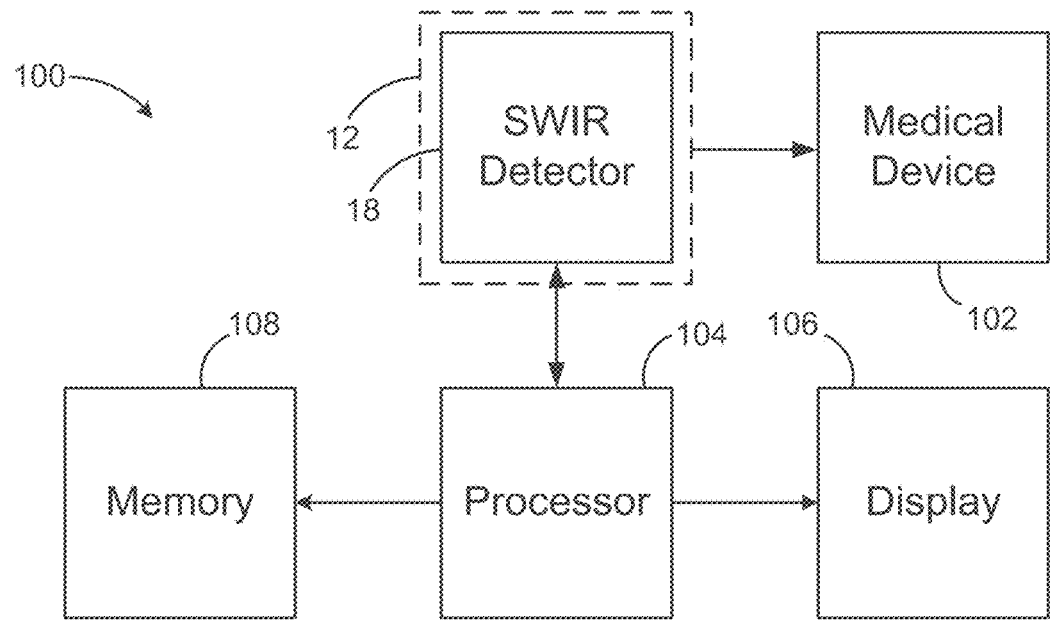
FIG. 4 shows a schematic block diagram of a short wave infrared system in accordance with one embodiment of the present disclosure.

FIG. 4 shows one non-limiting example of an SWIR system 100 in accordance with the present disclosure. As shown in FIG. 4, the SWIR retrofit kit 12 is configured to be integrated into a medical device 102 (e.g., the otoscope 14 or the endoscope 60). The SWIR detector 18 includes I/O ports 32, as described above, which enable the SWIR detector 18 to be connected to a processor 104. The processor 104 is in communication with a display 106 and a memory storage device 108. The processor 104 can be configured to control operating settings of the SWIR detector 18 (e.g., gain settings, array binning, exposure duration, etc.). Alternatively or additionally, the processor 104 can be configured to perform image processing algorithms on the images captured by the SWIR detector 18 to aid in detecting a malady of the patient's ear, as will be described below.

The display 106 can display images captured by the SWIR detector 18 for viewing by a medical professional. The memory storage device 108 can store images captured by the SWIR detector 18 to later viewing by a medical professional. In another non-limiting example, the memory storage device 108 can be a database of images captured using a plurality of medical devices 102.

One non-limiting example of operation of the SWIR otoscope device 10 when detecting the presence of middle ear fluid in a patient will be described with reference to FIGS. 1, 2, 4, 5, and 6A-C. When detecting middle ear fluid using the SWIR otoscope device 10, in one non-limiting example, the filter 36 can be a long pass filter configured to allow light with a wavelength of greater than approximately 1300 nm to transmit through the filter 36 to the SWIR detector 18, and the light source 16 can be configured to emit broadband SWIR light. The SWIR otoscope device 10 can be positioned by a medical professional such that the speculum 22 provides an optical path along the patient's ear canal. The light source 16 can then emit the broadband SWIR light along the optical path through the patient's tympanic membrane to illuminate the patient's middle ear. With the patient's middle ear illuminated by the broadband SWIR light of the light source 16, the plurality of optics 20 can focus, via the lens 40, the illuminated middle ear of the patient onto the SWIR detector 18.

Figure 5:
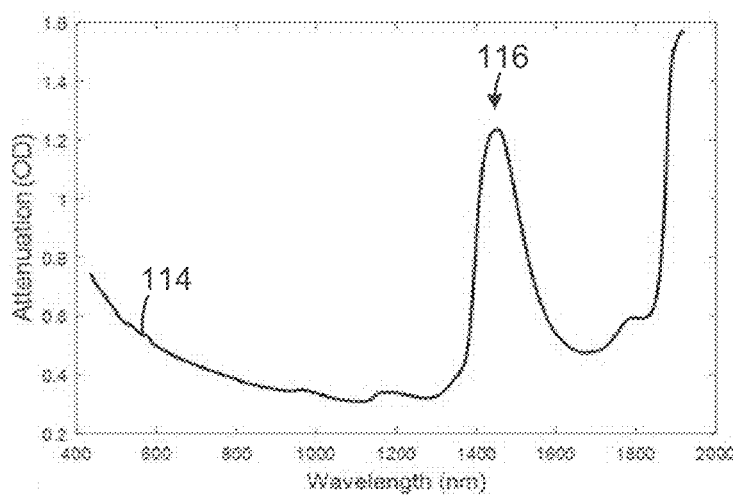
FIG. 5 shows a graph illustrating the attenuation of light traveling through middle ear fluid as a function of wavelength.

The medical professional can then instruct the processor 104 to capture one or more images, or a video, of the patient's illuminated middle ear with the SWIR detector 18 and display the images on the display 106. With the filter 36 arranged between the SWIR detector 18 and the lens 40, light with a wavelength greater than approximately 1300 nm will be detected/imaged by the SWIR detector 18. This combined with the broadband illumination of the light source 16 allows specific detection where absorption of middle ear fluid is elevated. As illustrated in the graph of FIG. 5, line 114 represents the relationship between attenuation (i.e., absorption and scattering of light) measured in optical density (O.D.) of middle ear fluid versus wavelength (nm). Line 114 shows elevated attenuation in the wavelength range beyond 1300 nm, as shown, for example by peak 116 on line 114. The lack of attenuation in the visible spectrum by middle ear fluid can lead to middle ear fluid appearing translucent in the visible wavelengths, whereas the strong absorption (shown by increased attenuation in line 114) of SWIR light causes middle ear fluid to appear black in an SWIR image. Therefore, the presence of middle ear fluid appears dark in an image captured by the SWIR detector 18. This allows for easy differentiation between the presence and absence of middle ear fluid without the need to rely on pneumatic-otoscope assessment of eardrum movement or the comparison of multiple wavebands.

Figure 6:
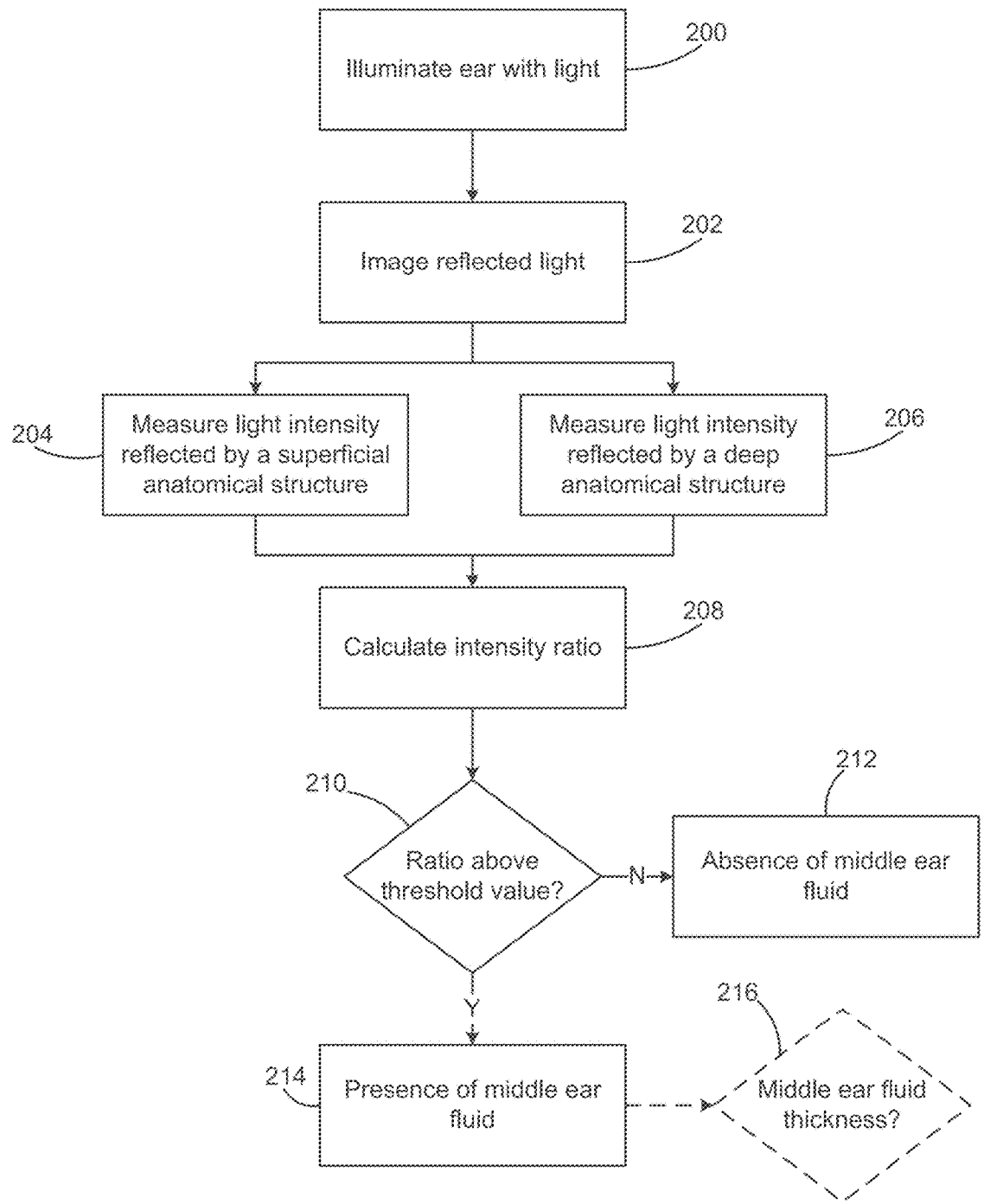
FIG. 6 is a flow chart illustrating steps for detecting a presence or absence of middle ear fluid in a patient using the SWIR otoscope system of FIG. 1.

The processor 104 may be configured to carry out image processing algorithms to supplement the differentiation between the presence and absence of middle ear fluid. FIG. 6 illustrates one non-limiting example of the steps for detecting middle ear fluid in a patient's ear using the SWIR otoscope device 10. Initially, at step 200, the light source 26 illuminates a patient's middle ear with SWIR light. In some non-limiting examples, the light source 26 may be configured to emit broadband SWIR light. In other non-limiting examples, the light source 26 may be configured to emit specific wavelengths of SWIR light, for example, to target water/middle ear fluid absorption bands. The light reflected from within the patient's middle ear can travel through the optical system 20. The reflected light traveling through the optical system 20 can be detected and imaged by the SWIR detector 18, at step 202. In some non-limiting examples, the filter 36 may be configured to transmit only wavelengths within water/middle ear fluid absorption bands to the SWIR detector 18. It should be appreciated that one or more images may be acquired of the reflected light from within the patient's middle ear.

Once the image is acquired at step 202, a light intensity of a superficial anatomical structure is measured at step 204. Simultaneously or subsequently, a light intensity of a deep anatomical structure is measured at step 206. In some non-limiting examples, the superficial anatomical structure may be the malleus or the external ear canal of the patient's ear. In some non-limiting examples, the deep anatomical ear structure may be the cochlear promontory. Once the intensities of the superficial and deep anatomical structures are measured at steps 204 and 206, an intensity ratio can be calculated between the measured intensity of the superficial anatomical structure and the measured intensity of the deep anatomical structure, at step 208. Once the intensity ratio is calculated at step 208, a determination is made at step 210 whether or not the calculated intensity ratio is above a predetermined threshold value. If the calculated intensity ratio is not determined to be above the predetermined threshold value, then the patient may have an absence of middle ear fluid, as indicated at step 212. In some non-limiting examples, if the intensity ratio is calculated to be approximately one, this may indicate that no fluid is present. Conversely, if the calculated intensity ratio is determined to be above the predetermined threshold value, then the patient may have fluid in their middle ear, as indicated at step 214. In some non-limiting examples, if the intensity ratio is calculated to be greater than approximately one, this may indicate fluid is present. Thus, the system and methods described herein enable differentiation between the presence and absence of middle ear fluid in a patient from a single acquired image. That is, the systems and methods described herein do not require the acquisition of multiple images in different absorption bands to detect the presence of middle ear fluid in a patient. This can enable the SWIR otoscope system 10 to more efficiently (i.e., faster due to reduced computational and system requirements) detect the presence of middle ear fluid in a patient.

Figure 7:
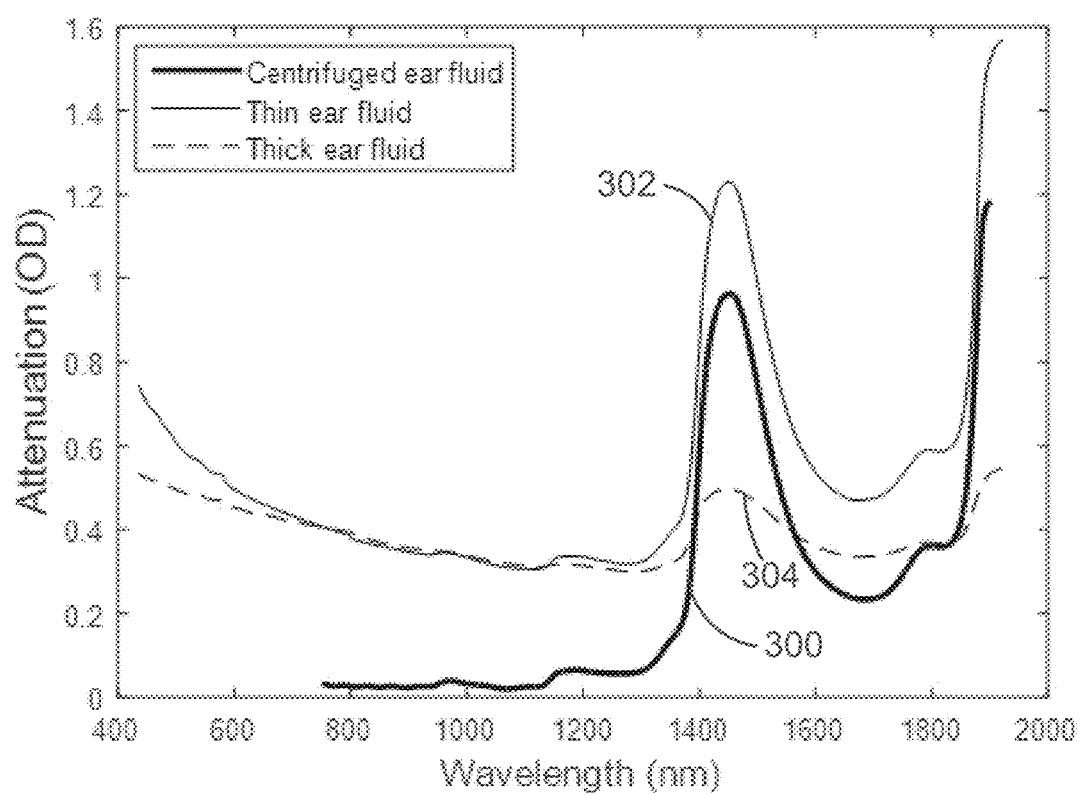
FIG. 7 is a graph illustrating attenuation as a function of wavelength for various thicknesses (i.e., viscosities) of middle ear fluid.

The calculation of the intensity ratio at step 208 may provide additional diagnostic capabilities to the SWIR otoscope system 10. With continued reference to FIG. 6, if it is determined that middle ear fluid is present at step 210, a value of the intensity ratio may further be applied to determine a thickness (i.e., a viscosity) of the detected middle ear fluid at step 216. That is, serous (thin) middle ear fluid and mucoid (thick) middle ear fluid can exhibit different absorption characteristics of SWIR light. For example, as shown in the graph of FIG. 7, thin (i.e., low viscosity) middle ear fluid (line 302) has a higher attenuation of SWIR light when compared with thick (i.e., high viscosity) middle ear fluid (line 304). Thus, the above-described process for determining the presence of middle ear fluid in a patient may further be applied to determine a thickness (i.e., a viscosity) of the detected middle ear fluid.

EXAMPLES

The following examples set forth, in detail, ways in which the SWIR otoscope device 10 and/or the SWIR retrofit kit 12 may be used or implemented, and will enable one of skill in the art to more readily understand the principles thereof. The following examples are presented by way of illustration and are not meant to be limiting in any way.

Figure 8A:
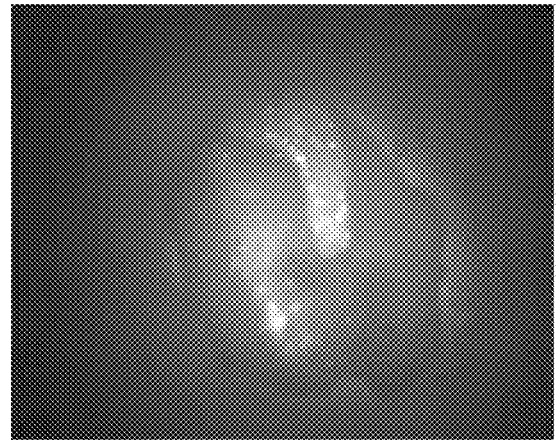
FIG. 8A illustrates a short wave infrared image of a middle ear model with no fluid taken using the short wave infrared otoscope device of FIG. 1.
Figure 8B:
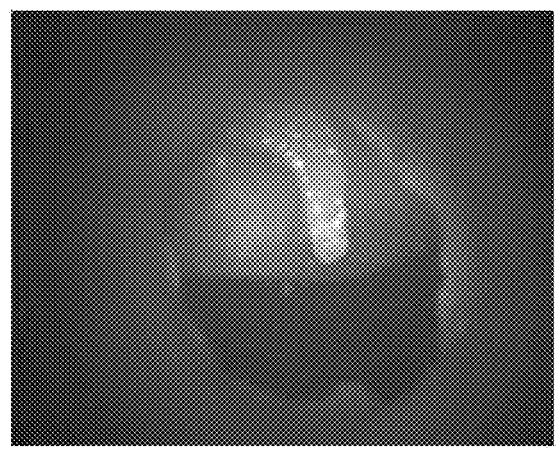
FIG. 8B illustrates a short wave infrared image of a middle ear model partially filled with fluid taken using the short wave infrared otoscope device of FIG. 1.
Figure 8C:
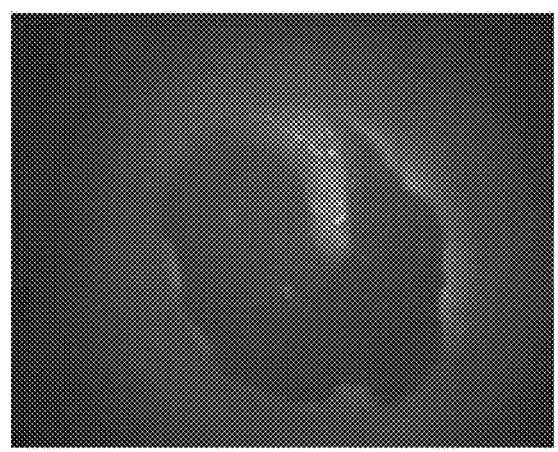
FIG. 8C illustrates a short wave infrared image of a middle ear model filled with fluid taken using the short wave infrared otoscope device of FIG. 1.

The detection of fluid using the SWIR otoscope device 10 in a middle ear model is illustrated in FIGS. 8A-8C. As shown in FIGS. 8A-8C there is a striking contrast between an SWIR image with fluid absent (FIG. 8A) and with fluid present (FIGS. 8B and 8C). The use of broadband SWIR illumination with the light source allows higher wavelength throughput to the SWIR detector 18 and, therefore, greater signal for imaging in the presence of significant absorption from the middle ear fluid. Thus, the SWIR otoscope device 10 can be used to aid a medical professional in diagnosing otitis media with effusion by unambiguously detecting the presence of middle ear fluid.

In another non-limiting example of detecting the presence of middle ear fluid using the SWIR otoscope device 10, the light source 16 may be configured to emit light in a wavelength range between 1300 nm and 1700 nm. It should be appreciated that alternative configurations of the filter 36 (i.e., long pass filter, short pass filter, or band pass filter that allow transmission of light above approximately 1300 nm) can be used to provide the dark contrast of the middle ear fluid in the images captured by the SWIR detector 18.

Another non-limiting example of operation of the SWIR otoscope device 10 when imaging the middle ear cavity of a patient will be described with reference to FIGS. 1, 2, 4, 7, and 8. In the absence of middle ear fluid, the SWIR otoscope device 10 can be used to image the middle ear cavity of a patient. When imaging the middle ear cavity, the light source 16 can be configured to emit broadband SWIR light, and the filter 36 may be removed to increase the amount of light transmitted to the SWIR detector 18. As described above, the lens 40 enables a high throughput (i.e., transmission) of SWIR light to the SWIR detector 18. This, in combination with removing the filter 36, can provide sufficient signal for imaging the entire middle ear cavity of the patient.

To achieve capturing images of the patient's middle ear cavity, the SWIR otoscope device 10 can be positioned by a medical professional such that the speculum 22 provides an optical path along the patient's ear canal. The light source 16 can then emit the broadband SWIR light along the optical path through the patient's tympanic membrane to illuminate the patient's middle ear cavity. With the patient's middle ear cavity illuminated by the broadband SWIR light of the light source 16, the plurality of optics 20 can focus, via the lens 40, the illuminated middle ear cavity of the patient onto the SWIR detector 18. The medical professional can then instruct the processor 104 to capture one or more images of the patient's illuminated middle ear cavity with the SWIR detector 18 and display the images on the display 106.

Figure 9:
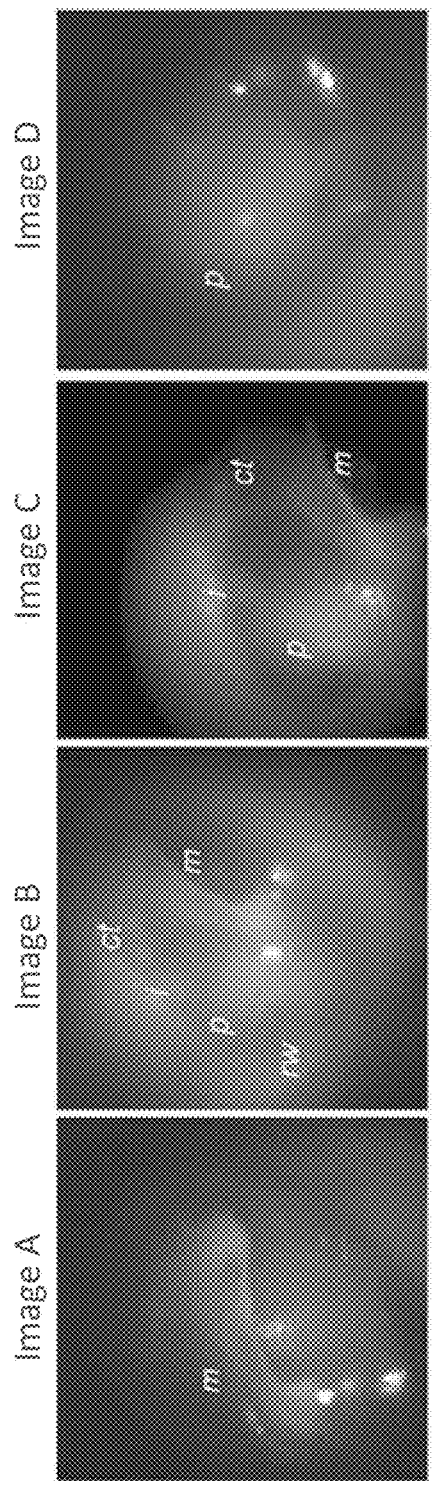
FIG. 9 illustrates four SWIR images (Images A-D) of the middle ear cavity of a patient's ear taken using the short wave infrared otoscope device of FIG. 1.
Figure 10:
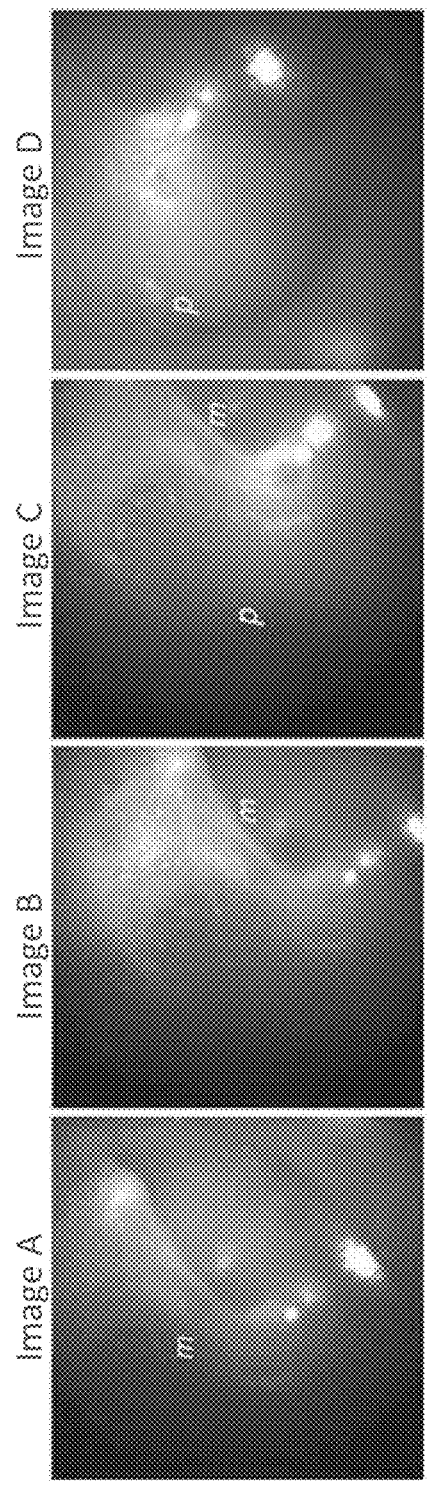
FIG. 10 illustrates four visible images (Images A-D) of the middle ear cavity of a patient's ear taken using visible light illumination and detection.

Imaging of a patient's middle ear cavity using the SWIR otoscope device 10 is illustrated in FIG. 9. As shown in Images A-D of FIG. 9, the malleus, promontory, round window, incudostapedial complex, and chorda tympani (indicated by m, p, rw, i, and ct in Images A-D of FIG. 9, respectively) are all identifiable using the SWIR otoscope device 10. Images A-D of FIG. 10 correspond with Images A-D of FIG. 9 but are captured using visible illumination and detection with a white LED light. As shown in FIG. 10, the tympanic membrane obstructs the promontory, round window, incudostapedial complex, and chorda tympani from view in Images A-D when compared with Images A-D of FIG. 9.

As shown in FIG. 9, the SWIR otoscope device 10 has the ability to image landmarks of the entire ossicular chain and the promontory in greater detail, which can be useful in evaluating conditions which result in conductive hearing loss, such as ossicular discontinuity and otosclerosis. The above described method of operation for imaging the middle ear cavity of a patient may be used to evaluate cholesteatoma extension within the middle ear of a patient, which can cause erosion of the ossicles or bony structures leading to hearing loss.

With continued reference to FIG. 9, the SWIR otoscope device 10 can clearly image the cochlear promontory, which is formed by the outward projection of the first turn of the cochlea against the posterior wall of the middle ear cavity. Clear visualization of the round window niche, one of the two openings from the middle ear to the inner ear, is also achieved. The round window is used as an insertion site for cochlear implant electrodes and for hearing aid transducers. Thus, the SWIR otoscope device 10 can be used to provide an alternative to radiographic imaging for evaluation of surgical implants.

Furthermore, the SWIR otoscope device 10 can image the chorda tympani, which is a branch of the facial nerve that carries sensation from the anterior two-thirds of the tongue. Due to the absorption of lipids around approximately 1210 nm, a filter 36 may be used to target the absorption of lipids and identify the chorda tympani based on the change in contrast. For example, the filter 36 may be a band pass filter with a center wavelength between approximately 1200 nm and 1220 nm.

As described above, the SWIR retrofit kit 12 can be easily integrated into the otoscope 14 to form the SWIR otoscope device 10 which can be used to image and aid in the detection of one or more maladies of a patient's ear.

Thus, while the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein.

We claim:

1. A short wave infrared otoscope device comprising:
   a light source configured to emit short wave infrared light along an optical path through a speculum to illuminate a two-dimensional portion of a patient's ear with short wave infrared light;
   a short wave infrared detector configured to be coupled to a speculum adapter to receive reflected light from the two-dimensional portion of the patient's ear and generate a two-dimensional image of the two-dimensional portion of a patient's ear; and
   an optical system arranged between the speculum and the short wave infrared detector, the optical system including a lens.

2. The short wave infrared otoscope device of claim 1, wherein the light source is fiber-coupled.

3. The short wave infrared otoscope device of claim 1, wherein the light source includes one or more light emitting diodes.

4. The short wave infrared otoscope device of claim 1, wherein the light source is an incandescent or tungsten-halogen light source.

5. The short wave infrared otoscope device of claim 1, wherein the two-dimensional portion of the patient's ear is a middle ear.

6. The short wave infrared otoscope device of claim 1, wherein the optical system further comprises only one filter.

7. The short wave infrared otoscope device of claim 6, wherein the only one filter is configured to transmit light with a wavelength greater than approximately 1300 nanometers.

8. The short wave infrared otoscope device of claim 1, wherein the optical system further comprises a first polarizer.

9. The short wave infrared otoscope device of claim 8, wherein the optical system further comprises a second polarizer.

10. The short wave infrared otoscope device of claim 9, wherein the first polarizer is arranged adjacent to the short wave infrared detector and the second polarizer is arranged adjacent to the light source.

11. The short wave infrared otoscope device of claim 9, wherein the first polarizer and the second polarizer are near-infrared linear polarizers.

12. The short wave infrared otoscope device of claim 1, wherein the lens is a near-infrared achromatic lens pair.

13. The short wave infrared otoscope device of claim 12, wherein the achromatic lens pair includes a 75 millimeter effective focal length lens and a 100 millimeter effective focal length lens.

14. A short wave infrared retrofit kit for an otoscope having a speculum received within a speculum adapter, the short wave infrared retrofit kit comprising:
   a light source configured to emit short wave infrared light through the speculum to illuminate a two-dimensional portion of a patient's ear;
   a short wave infrared detector configured to be coupled to the speculum adapter and arranged to view through the speculum, wherein the short wave infrared detector is configured to capture a two-dimensional image through the speculum of the two-dimensional portion of the patient's ear; and
   an optical system arranged between the speculum and the short wave infrared detector, the optical system including a lens.

15. The short wave infrared retrofit kit of claim 14, wherein the light source is fiber-coupled.

16. The short wave infrared retrofit kit of claim 14, wherein the light source includes one or more light emitting diodes.

17. The short wave infrared retrofit kit of claim 14, wherein the light source is an incandescent or tungsten-halogen light source.

18. The short wave infrared retrofit kit of claim 14, wherein the optical system further comprises only one filter.

19. The short wave infrared retrofit kit of claim 18, wherein the only one filter is configured to transmit light with a wavelength greater than approximately 1300 nanometers.

20. The short wave infrared retrofit kit of claim 14, wherein the optical system further comprises a first polarizer.

21. The short wave infrared retrofit kit of claim 20, wherein the optical system further comprises a second polarizer.

22. The short wave infrared retrofit kit of claim 21, wherein the first polarizer is arranged adjacent to the short wave infrared detector and the second polarizer is arranged adjacent to the light source.

23. The short wave infrared retrofit kit of claim 21, wherein the first polarizer and the second polarizer are near-infrared linear polarizers.

24. The short wave infrared retrofit kit of claim 14, wherein the lens is a near-infrared achromatic lens pair.

25. The short wave infrared retrofit kit of claim 24, wherein the achromatic lens pair includes a 75 millimeter effective focal length lens and a 100 millimeter effective focal length lens.

26. A method for using a short wave infrared device to detect a malady of a patient's ear, the short wave infrared device including a light source, a short wave infrared detector arranged to view along an optical path, and an optical system arranged along the optical path, the method comprising:
   positioning the short wave infrared detector to view within the patient's ear;
   emitting short wave infrared light along the patient's ear canal via the light source;
   illuminating a two-dimensional portion of the patient's ear via the emitted short wave infrared light;
   capturing a two-dimensional image, using the short wave infrared detector, of the reflected light from the illuminated two-dimensional portion of the patient's ear; and
   detecting the malady of the patient's ear based on an abnormality in the captured image.

27. The method of claim 26, further comprising:
   filtering light reflected from the illuminated two-dimensional portion of the patient's ear prior to the reflected light reaching the short wave infrared detector.

28. The method of claim 27, wherein filtering light reflected from the illuminated two-dimensional portion of the patient's ear comprises:
   transmitting only light with a wavelength greater than approximately 1300 nanometers.

29. A method for retrofitting an otoscope with a short wave infrared retrofit kit, the otoscope including a speculum received within a speculum adapter, the method comprising:
coupling a light source to the speculum adapter, the light source configured to emit short wave infrared light through the speculum to illuminate a two-dimensional portion of a patient's ear;
coupling a short wave infrared detector to the speculum adapter, the short wave infrared detector arranged to view through the speculum and capture a two-dimensional image through the speculum of the two-dimensional portion of the patient's ear; and
arranging an optical system between the speculum and the short wave infrared detector, the optical system including a lens.

30. A method for detecting fluid in a middle ear of a patent, the method comprising:
illuminating a portion of the patient's ear with short wave infrared light;
detecting light reflected from the portion of the patients ear with a short wave infrared detector and acquiring an image of the detected light;
measuring a light intensity of a superficial anatomical structure in the acquired image;
measuring a light intensity of a deep anatomical structure in the acquired image;
calculating an intensity ratio between the light intensity of the superficial anatomical structure and the light intensity of the deep anatomical structure;
determining if the calculated intensity ratio is above a predetermined threshold value; and
upon determining that the calculated intensity ratio is above the predetermined threshold value, detecting a presence of fluid in the middle ear of the patient.

31. The method of claim 30, wherein illuminating a portion of the patient's ear with short wave infrared light comprises:
emitting broadband short wave infrared light from a light source in a wavelength range between 800 nanometers and 2000 nanometers.

32. The method of claim 30, wherein illuminating a portion of the patient's ear with short wave infrared light comprises:
emitting short wave infrared light from a light source at a wavelength that is absorbed by water or middle ear fluid.

33. The method of claim 30, wherein measuring a light intensity of a superficial anatomical structure in the acquired image comprises:
measuring a light intensity at a malleus of the patient's ear in the acquired image.

34. The method of claim 30, wherein measuring a light intensity of a superficial anatomical structure in the acquired image comprises:
measuring a light intensity at an external ear canal of the patient's ear in the acquired image.

35. The method of claim 30, wherein measuring a light intensity of a deep anatomical structure in the acquired image comprises:
measuring a light intensity at a cochlear promontory of the patient's ear in the acquired image.

36. The method of claim 30, further comprising:
upon determining that the calculated intensity ratio is below the predetermined threshold value, indicating an absence of fluid in the middle ear of the patient.

37. The method of claim 30, further comprising:
determining a viscosity of the detected middle ear fluid based on a value of the calculated intensity ratio.

* * * * *